United States Patent [19]
Hakky et al.

[11] Patent Number: 6,096,013
[45] Date of Patent: Aug. 1, 2000

[54] COLLAPSIBLE URINARY CATHETER

[75] Inventors: Said I. Hakky; A-Hamid Hakki, both of Largo, Fla.

[73] Assignee: Canox International Ltd., Largo, Fla.

[21] Appl. No.: 09/262,605

[22] Filed: Mar. 4, 1999

[51] Int. Cl.[7] .................................................. A61F 5/44
[52] U.S. Cl. ............................................ 604/349; 604/544
[58] Field of Search ............................... 604/96, 97, 103, 604/264, 530, 319, 327–329, 349, 544

[56] References Cited

U.S. PATENT DOCUMENTS 5,183,464  2/1993  Dubrul et al. ........................ 604/96 X
5,735,831  4/1998  Johnson et al. ..................... 604/264 X

*Primary Examiner*—Wynn Wood Coggins
*Assistant Examiner*—A. T. Nguyen
*Attorney, Agent, or Firm*—Rosenberg, Klein & Lee

[57] ABSTRACT

A collapsible hollow elastomeric tube catheter for draining the urinary bladder. The wall of the collapsible catheter is constructed of minimally distensible, or non-distensible, biocompatible rubber material. Fluid may be injected in the catheter wall to cause stiffening of the catheter when desired, such as during insertion into the bladder. The proximal end of the catheter has a retaining mechanism within the urinary bladder without the use of a balloon.

11 Claims, 9 Drawing Sheets

COLLAPSIBLE URINARY CATHETER

BACKGROUND OF THE INVENTION

1. Field of the Invention

This invention relates generally to the field of surgical devices and, more particularly, to a collapsible indwelling catheter for draining the urinary bladder, with the proximal part of the collapsible catheter being self retaining inside the urinary bladder.

2. Description of the Prior Art

A urinary bladder tube is used in certain patients who have undergone major surgery, or any patient who is unable to urinate. There are many causes for inability to urinate. These causes differ with age and sex. For example, a small child may not urinate because of some congenital abnormality obstructing the bladder neck or urethra. In females, inability to urinate occurs in neurological diseases, after delivery of a baby, or after major abdominal or pelvic surgery. In a male, the most common causes of inability to urinate are an obstructing prostate, neurological diseases, or after major abdominal or pelvic surgery.

It is desirable to continuously drain the bladder after major surgery at least for the purpose of monitoring the hourly urine output. It is also desirable to continuously drain the bladder by an indwelling Foley catheter in medical conditions where the measurement of hourly urine output is important to the well being of the patient.

It is also important to drain the bladder by an indwelling catheter after prostate or bladder surgery. Diverting the urine and blood will promote fast healing and prevent clots from building up in the bladder, which often cause more bleeding and severe pain.

In certain bladder or prostate surgeries, a continuous bladder irrigation is used. This is achieved by injecting fluid continuously into the bladder and simultaneously draining the bladder. This type of Foley catheter is called a three-way catheter. One port will serve as fluid injection port into the bladder. The second port is for continuous drainage of the bladder content into a large urine bag. The third port is for a valve mechanism where a balloon is inflated inside the bladder to keep the tip of the Foley catheter indwelling inside the bladder.

In certain patients, the bladder must be drained for many years, such as debilitated patients or those with neurological or spinal cord lesions. If the bladder is not drained, the pressure in the bladder will build up and the kidneys will be obstructed. Continuous bilateral kidney obstruction may lead to renal failure in a few weeks.

Therefore, the use of an indwelling catheter is very important, and could be life-saving, both in an acute and chronic long term settings.

There are many serious drawbacks to the standard rigid indwelling Foley catheter. This standard catheter must be stiff enough to be introduced into the bladder, and, as such, will continuously stretch the urethra as long as the catheter is indwelling. Continuously stretching the urethra is painful, and certain patients cannot tolerate the catheter because of the severe pain. The human urethra is always in a state of collapse except during urination, and, in the male, during ejaculation as well. Continuous stretching of the urethra is painful and may produce urethritis or urinary tract infection. A patient is given medications, sedation, and even narcotics to ease the bladder and urethral painful spasms from the rigid indwelling Foley catheter.

Thus, it is ideal if a Foley catheter has enough rigidity to be introduced, then the stiffness be replaced by softness. This could be achieved by a catheter with walls that are rigid when desired and then made soft when desired. Such a catheter would mimic the urethra in the physiological status. The pain or discomfort from an indwelling catheter will then be minimized. In addition, urethral irritation will be minimized, thus lowering the incidence of urinary tract infection.

SUMMARY OF THE INVENTION

Accordingly, it is an object of the present invention to provide a collapsible hollow tube which mimics the urethra in every respect, thus overcoming the disadvantages of the prior art.

It is a further object of the present invention to provide a hollow tube and method of aspirating the bladder after surgery, and in certain medical conditions.

It is still a further object of the present invention to provide a hollow tube and method of irrigating the bladder in certain urological conditions.

It is a further object of the present invention to provide a hollow tube that can be rigid when desired and also return to the state of flaccidity when desired, thus duplicating the physiological status of the urethra.

It is yet a further object of the present invention that the tip of the catheter be closed when introduced into the bladder.

It is still a further object of the present invention that the tip of the catheter will open using thin plastic memory rods, without the use of a balloon, maintaining the proximal end of the catheter inside the urinary bladder.

It is yet a further object of the present invention that the tip of the catheter will open under fluid pressure to maintain the proximal end of the catheter inside the bladder.

These and other objects and advantages of the present invention will be more readily apparent in the description that follows.

DETAILED DESCRIPTION OF THE PREFERRED EMBODIMENTS

Figure 7:
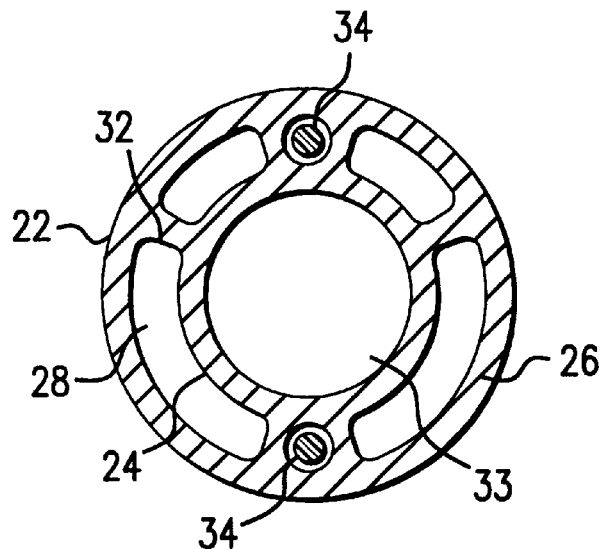
FIG. 7 is a cross-sectional view taken along line 7—7 of FIG. 1.

Referring now to the drawings, a collapsible catheter, generally designated at 10, which embodies the principles of the present invention is shown. Catheter 10 consists of a hollow tube 12 having a proximal end 14 and a distal end 16. In the present embodiment, catheter 10 is preferably 30 to 35 centimeters in length and approximately 10 millimeters in diameter. Proximal end 14 terminates in a pair of opposed end sections 18, 20 which form a closed end in FIG. 1. Distal end 16 is formed from a hollow, relatively rigid non-collapsible tube 21. Distal end 16, which is open, can also accommodate the attachment of a urine bag (not shown), and can also be used for manual irrigation of the bladder to remove blood clots or debris. A central portion 22 of catheter 10 is located between proximal end 14 and distal end 16 and is preferably constructed from two coaxial thin non-distensible or minimally distensible biocompatible rubber tubes 24, 26 (FIG. 7). Tubes 24 and 26 are separated by a chamber 28 (FIG. 7) which extends distally to a valve mechanism 30 which supplies fluid pressure to central portion 22 of catheter 10 via chamber 28 to stiffen portion 22. Tube 24, which is located within tube 26, is maintained at a fixed distance from outer tube 26 by a plurality of wall sections 32. Thus, if chamber 28 is pressurized, inner tube 24 will not collapse, which collapse could possibly obstruct the flow of urine within a channel 33 inside of tube 24.

When catheter 10 is in use, proximal end 14 is located within the urinary bladder, central portion 22 is located within the urethra, and distal end 16 lies outside the urethra. In order to maintain catheter 10 in its proper position within the bladder, a pair of plastic rods 34 are located within a pair of corresponding channels 35 located on opposite sides along the length of catheter 10 and extend beyond distal end 16.

Each of plastic rods 34 contains a memory section 36. As rods 34 are shifted toward proximal end 14, memory sections 36 cooperate with a pair of corresponding memory sections 38 within central portion 22 of catheter 10 (see FIGS. 2–5) to force end sections 18 and 20 apart, thus retaining proximal end 14 within the urinary bladder.

Figure 8:
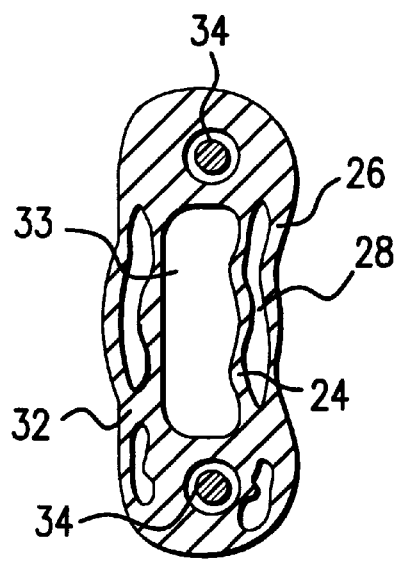
FIG. 8 is a view of the catheter shown in FIG. 7 in the collapsed position.

In order to introduce catheter 10 into the bladder of a patient, it must be sufficiently rigid to be inserted. To accomplish this, water is injected through valve mechanism 30 into chamber 28. The injection of a minimal amount of water, which is a non-compressible fluid, into chamber 28 will quickly pressurize this chamber, changing the wall of central portion 22 from a soft wall to a rigid wall, due to the non-distensible property of tubes 24 and 26, as the tubes, which are constructed from a minimally distensible (or non-distensible) rubber material, will resist distension when pressurized, resulting in a steep rise in the pressure in chamber 28. Thus, central portion 22 of catheter 10 changes from a soft collapsible state (FIG. 8) to a rigid (or even hard) state (FIG. 7).

Once catheter 10 is rigid, it is then introduced inside the bladder, and urine will pass through channel 33 and appear at distal end 16, indicating that proximal end 14 is within the bladder. At this time, rods 34 are advanced toward proximal end 14 to separate end sections 18 and 20 inside the bladder wall, thus securing catheter 10 in position within the bladder. This is a significant improvement over the standard Foley catheter, which requires a balloon mechanism along with a valve mechanism for operation, often causing pain and spasm within the bladder of the patient, and, if the balloon is accidentally inflated inside the urethra, may cause urethral injury and bleeding.

Once catheter 10 is in its proper position, then fluid within central portion 22 is reduced, thus decreasing the pressure within chamber 28, and changing the wall stiffness from rigid to flaccid. The degree of stiffness can be adjusted by the amount of fluid aspirated. If all of the fluid is removed, catheter 10 will conform to the shape of the normally collapsed urethra.

If it is necessary that blood clots or debris are to be evacuated from the bladder, the wall of catheter 10 can be repressurized to stiffen tubes 24 and 26 sufficiently in order to prevent collapse of tube 24 onto channel 33 upon aspirating the bladder content. In rare cases, central portion 22 must be rigid, rather than firm, to help aspirate and break any large clots from the bladder cavity. This procedure is not possible with the standard Foley catheter, as the patient must be taken to an operating room to evacuate the clots using a cystoscope. The present invention thus can maintain a rigid wall, a firm wall, and a soft collapsible wall as desired.

Once the urine from the bladder becomes clear or there is no need for a firm or a rigid catheter, then the fluid from chamber 28 is aspirated, decreasing the pressure within central portion 22 of catheter 10, allowing portion 22 to conform to the shape of the surrounding normally collapsed urethra.

Figure 1:
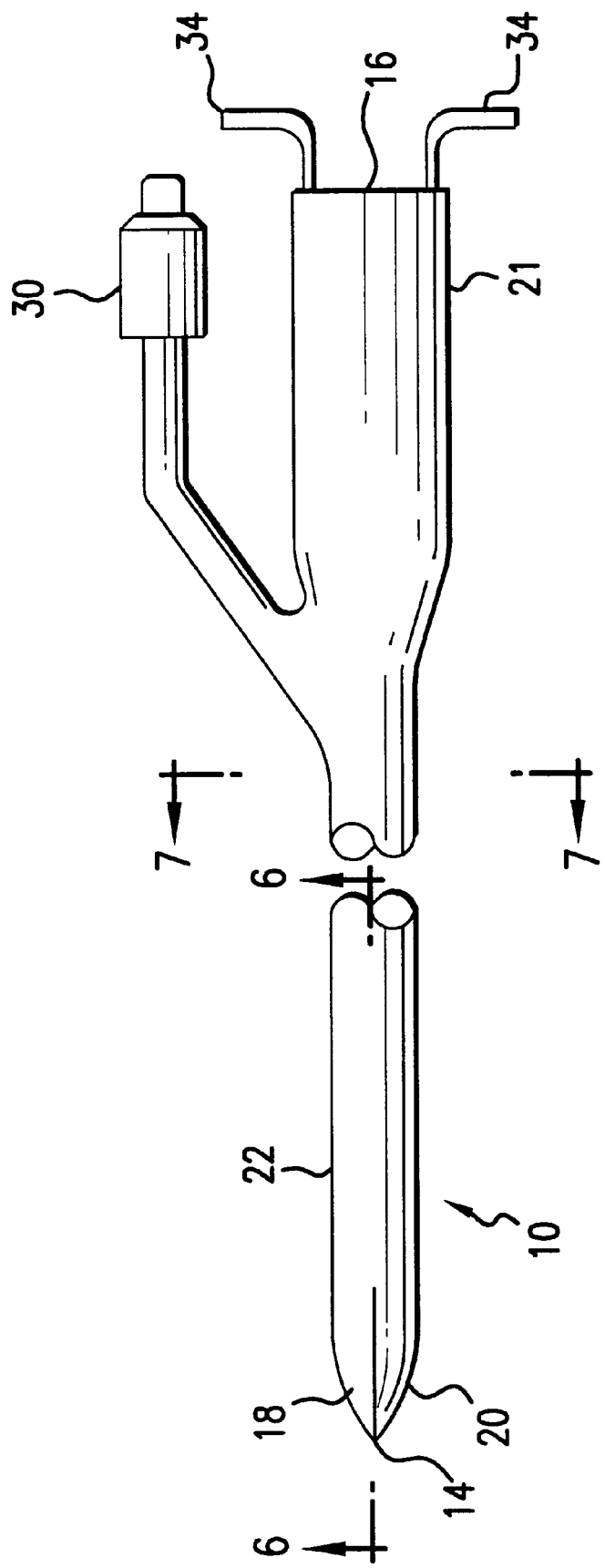
FIG. 1 is a fragmentary side elevational view of an embodiment of a unitary catheter according to the present invention.
Figure 2:
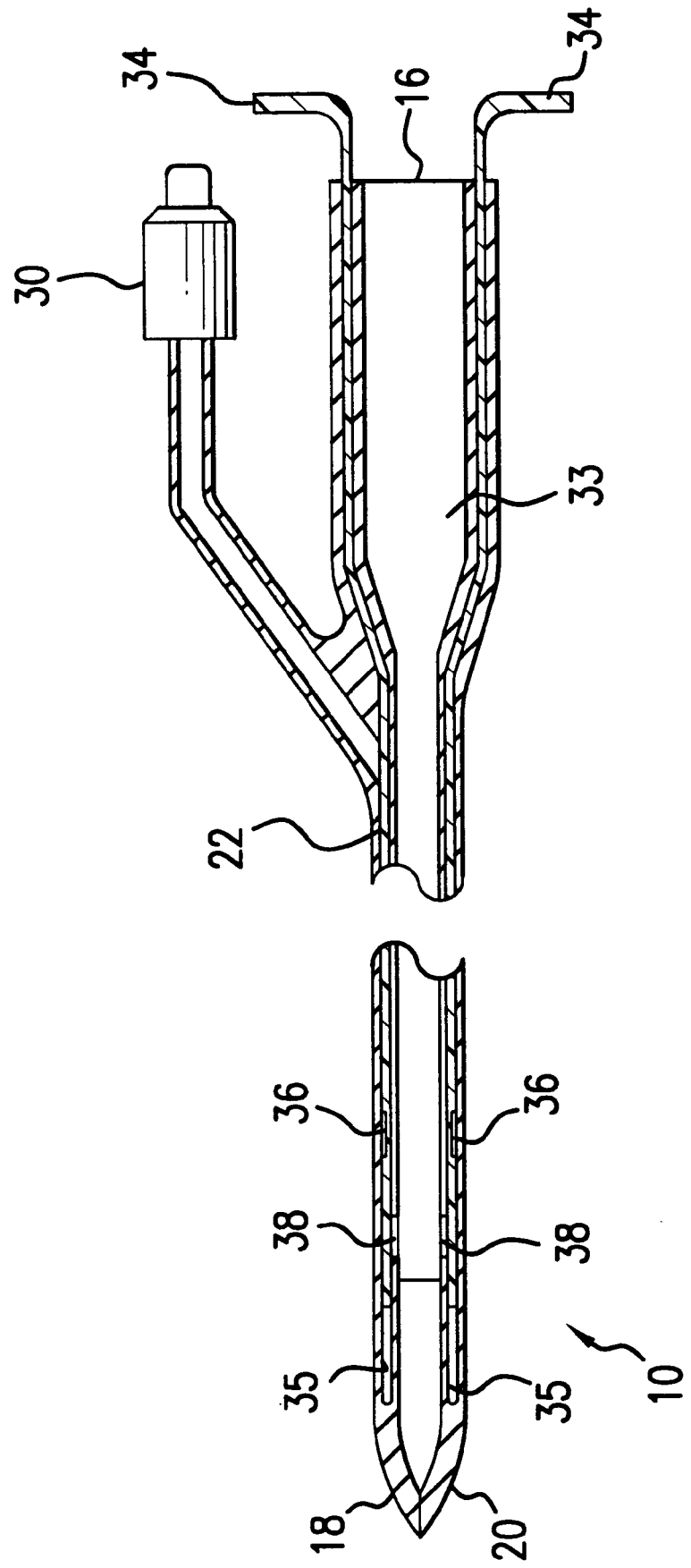
FIG. 2 is a cross-sectional view of the catheter shown in FIG. 1.
Figure 3:
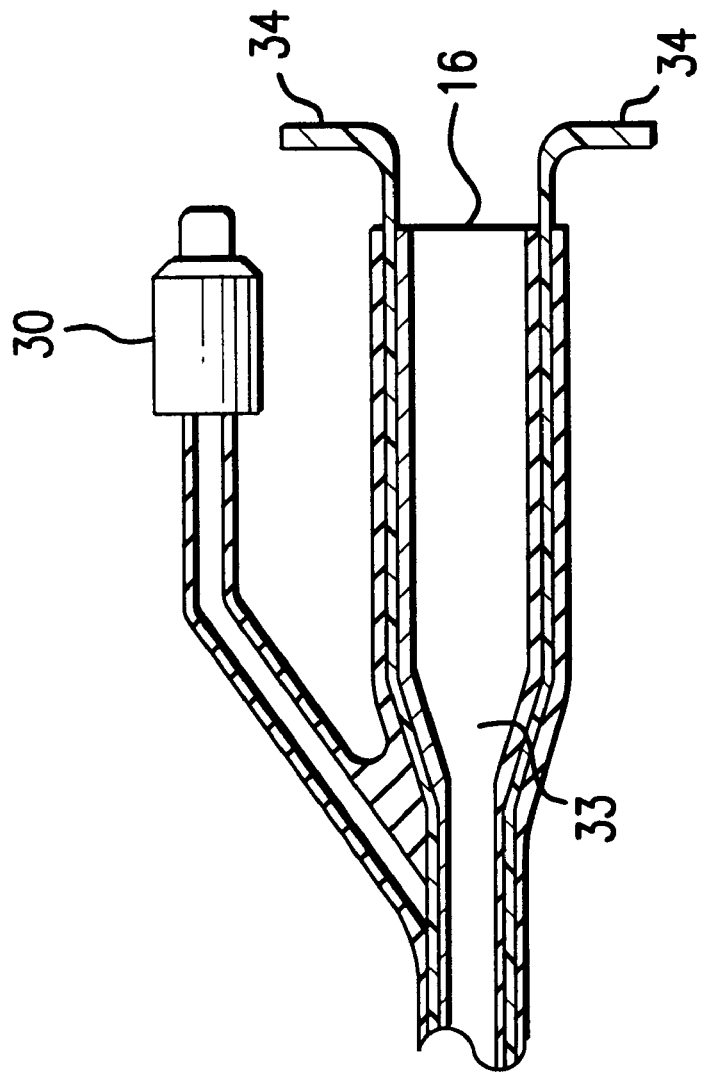
FIG. 3 is a cross-sectional view of the catheter shown in FIG. 1 with the retaining mechanism at the tip in the activated position.
Figure 4:
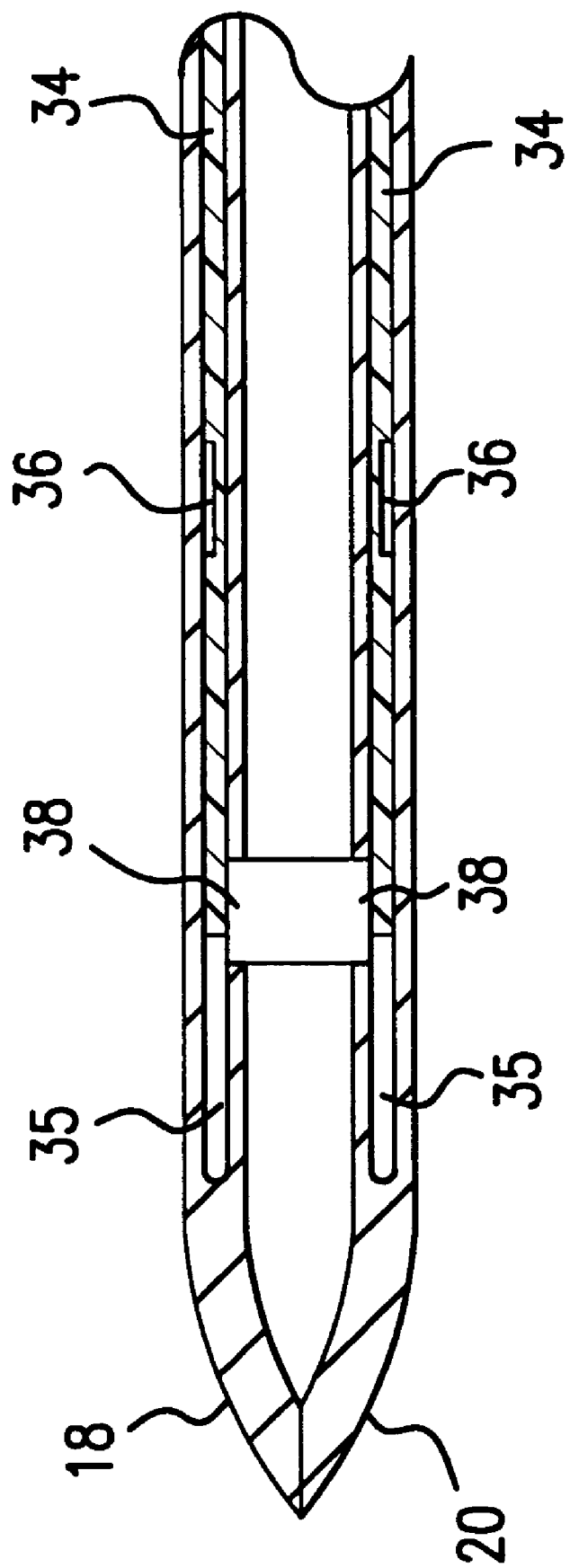
FIG. 4 is an exploded view of the catheter tip shown in FIG. 3.
Figure 5:
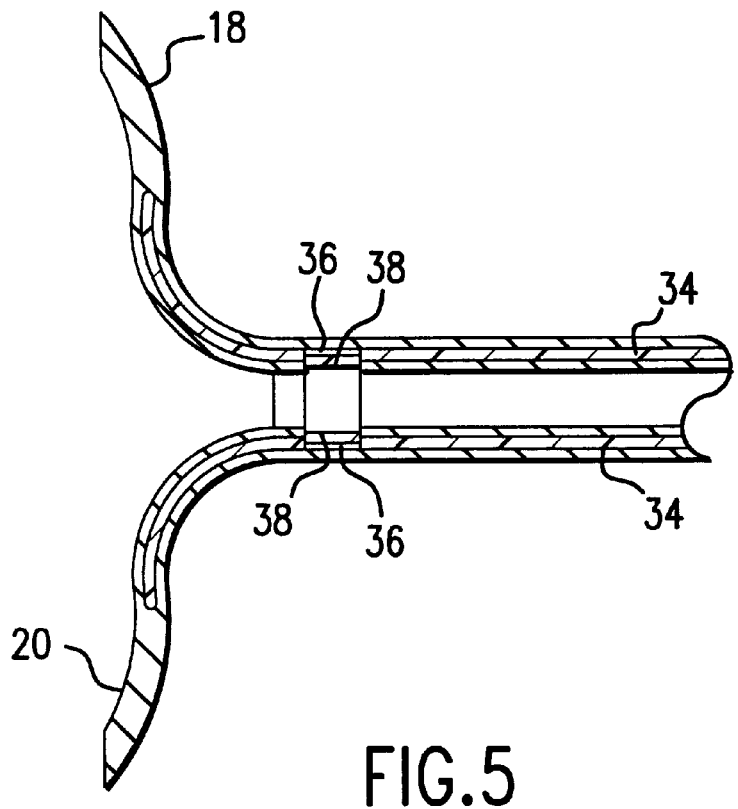
FIG. 5 is an exploded view of the catheter tip shown in FIG. 2.
Figure 6:
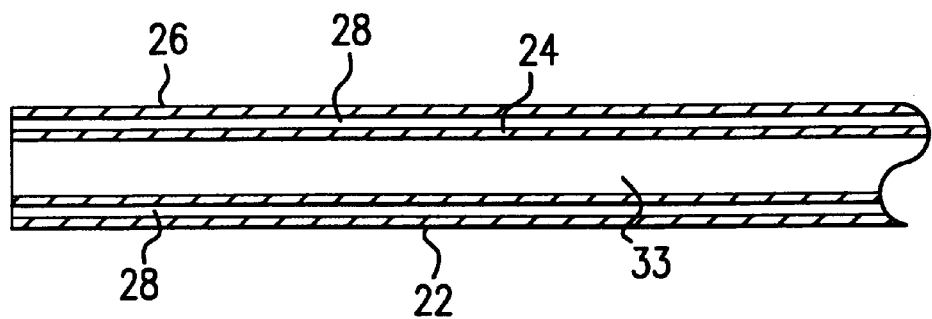
FIG. 6 is an exploded view taken along line 6—6 of FIG. 1 with the plastic rods removed to more clearly illustrate the inflatable/collapsible part of the catheter.

Removal of catheter 10 is accomplished by shifting rods 34 toward distal end 16 to the unactivated position shown in FIGS. 1 and 2. This action will return sections 18 and 20 to the closed position shown in these figures. Catheter 10 can then be easily withdrawn from the bladder and urethra.

Under certain conditions, an additional hollow tube may be added to catheter 10. This tube, which is also made of collapsible material, is connected to an outside reservoir of fluid for irrigation. This device is useful when the patient is bleeding continuously from the kidneys, bladder, or prostate, and prevents clotting of the blood inside the bladder, which is extremely painful.

Figure 9:
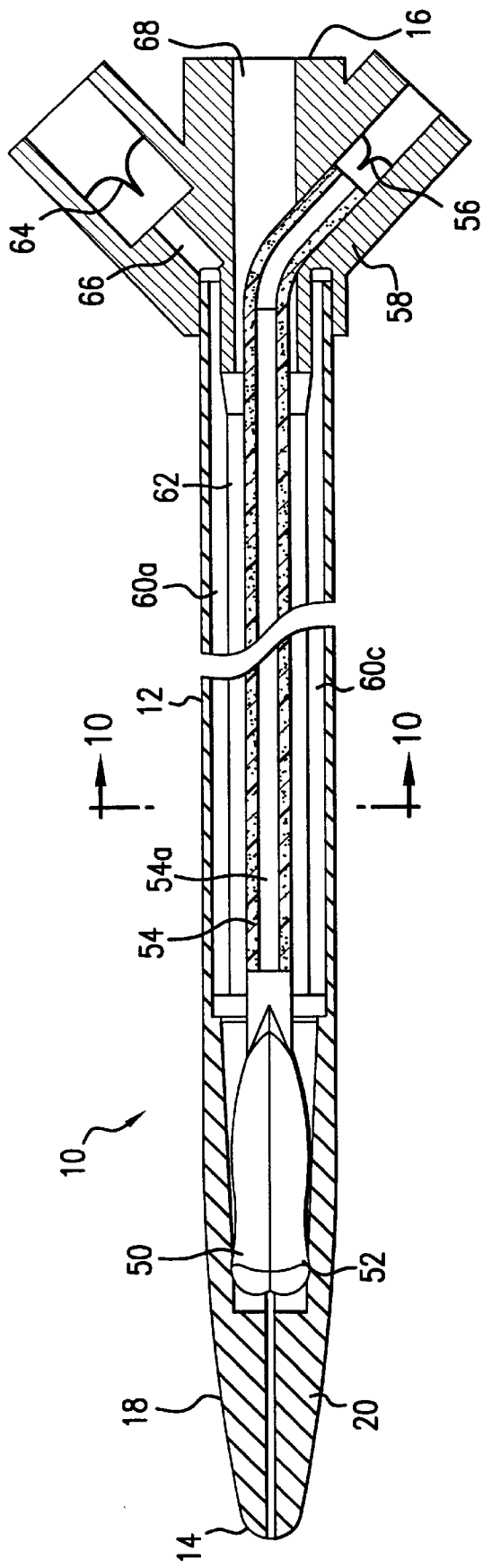
FIG. 9 shows, in fragmentary cross section, an alternative embodiment of the urinary catheter of the present invention; in its uninstalled state.
Figure 10:
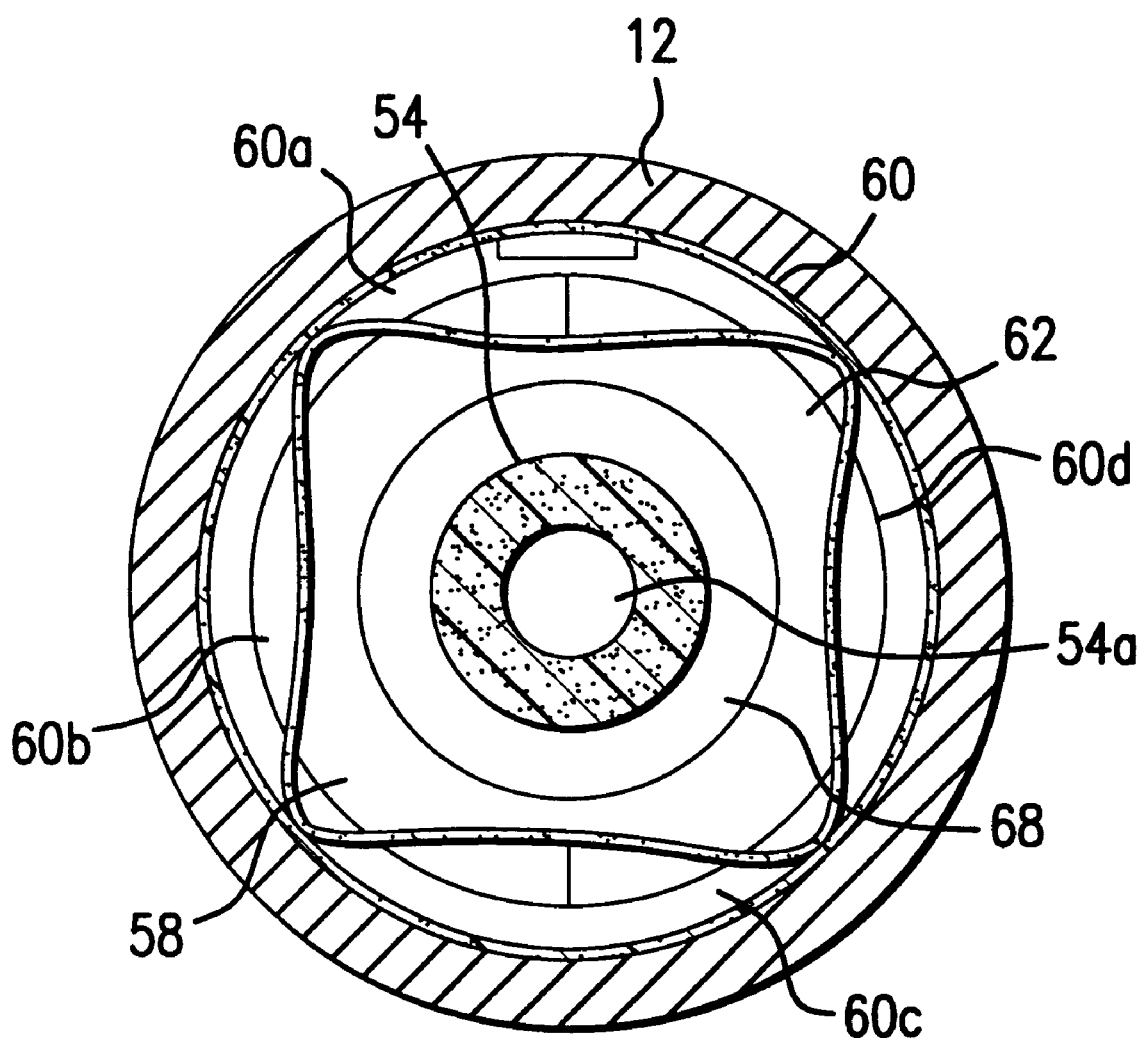
FIG. 10 is a cross-sectional view taken along line 10—10 of FIG. 9.
Figure 11:
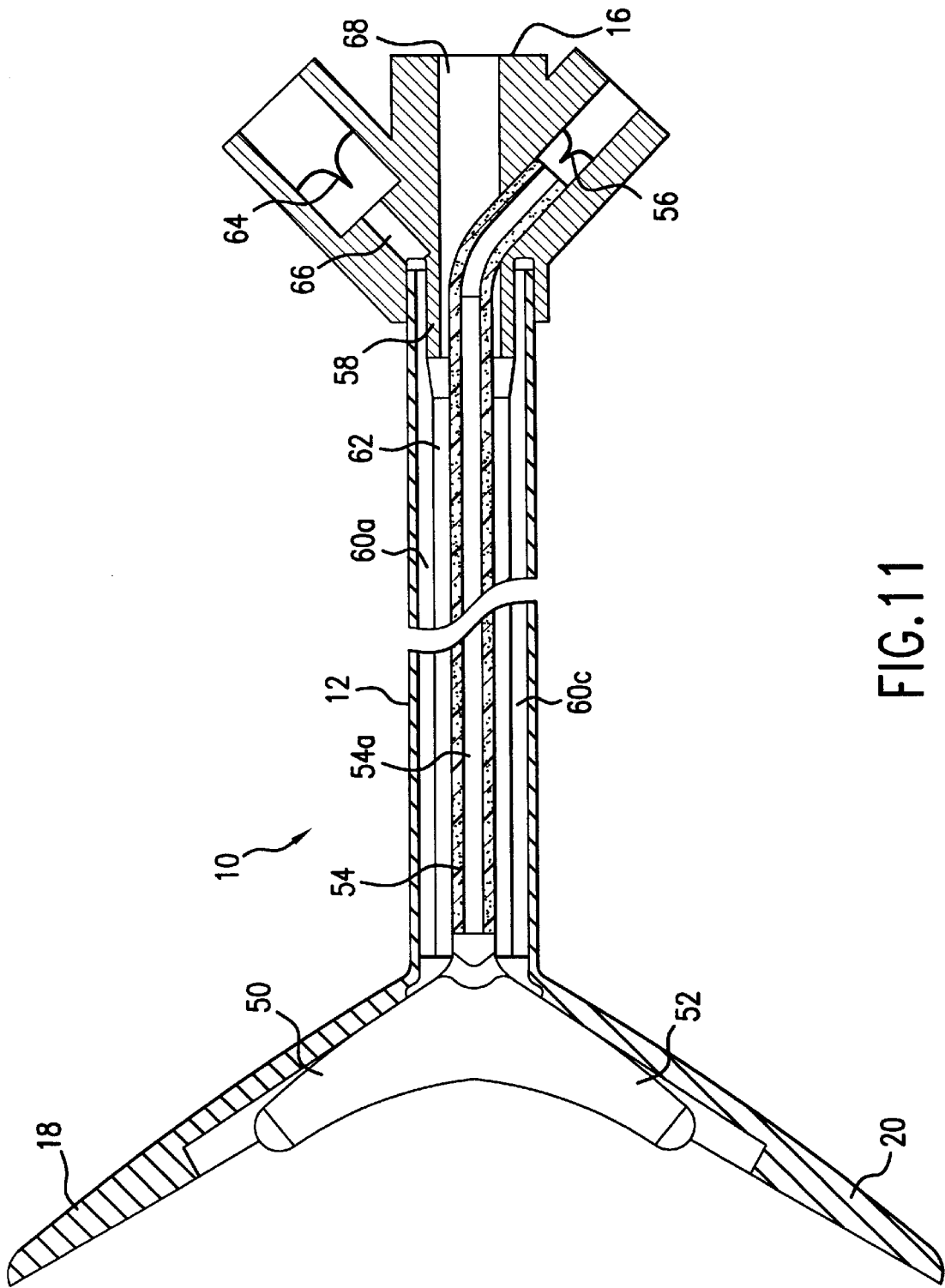
FIG. 11 is a cross-sectional view of the device shown in FIG. 9 in its installed state.

FIGS. 9–11 serve to illustrate an alternative embodiment of the present invention. It will be appreciated that, in this embodiment, similar parts are given the same numerals as the first embodiment.

Referring now to FIG. 9, catheter 10 consists of an outer hollow body 12 having a proximal end 14 and a distal end 16. Body 12 is preferably constructed from silicone. Proximal end 14 terminates in a pair of opposed end sections 18, 20, which are in apposition when catheter 10 is in the uninstalled position shown in FIG. 9. Affixed to the inner surfaces of sections 18 and 20 near proximal end 14 of catheter 10 are a pair of expandable chambers 50 and 52, respectively. Chambers 50 and 52, which are preferably constructed from a flexible polyurethane, are coupled to a hollow silicone tube 54 which extends along the length of catheter 10. Tube 54, which has an interior chamber 54a, terminates near distal end 16 of catheter 10 at a check valve 56 extending outwardly from body 12, which is housed in a connector 58.

Also located within outer body 12 of catheter 10 is a multiple lumen tube 60. Tube 60, which is manufactured from a non-distensible material such as polyurethane, extends from sections 18 and 20 along the length of catheter 10, terminating at connector 58. Tube 60 contains a plurality of chambers 60a, 60b, 60c, and 60d which are situated about a central passageway 62. The interior spaces of chamber 60a, 60b, 60c and 60d communicate with a check valve 64, which extends outwardly from body 12 and is located within connector 58, via a channel 66. Central passageway 62 extends from sections 18 and 20 at proximal end 14 to connector 58, where passageway 62 communicates with the exterior of catheter 10 at distal end 16 via a channel 68.

To insert catheter 10 into the bladder of a patient, it must sufficiently rigid to be inserted through the urethra. To accomplish this, a syringe containing a saline solution, or any compatible fluid, is inserted into check valve 64 of connector 58 and activated, introducing the solution through channel 66 and into chambers 60a, 60b, 60c, 60d and tube 60. As tube 60 is constructed from non-distensible material, the increasing pressure generated by the solution causes tube 60 to become rigid. In this rigid state, catheter 10 can now be inserted through the urethra into the bladder. In this position, urine within the bladder drains through passageway 62 and channel 68 to exterior of catheter 10 at distal end 16.

When catheter 10 has been properly positioned with the bladder, a syringe may be inserted into check valve 56 of connector 58 to inject saline solution or any compatible fluid through interior chamber 54a of tube 54 into chambers 50 and 52. As chambers 50 and 52 are filled with the saline solution, they expand and separate, causing sections 18 and 20 extend in opposite directions, thus retaining catheter 10 in its indwelling position.

The rigidity of catheter 10 can be adjusted by adjusting the fluid pressure within tube 50 via check valve 64 and a syringe.

To remove catheter 10, a syringe is attached to check valve 56 in connector 58, removing the fluid solution from tube 54 and chambers 50 and 52, thus allowing sections 20 and 22 to return to the uninstalled position as shown in FIG. 9. Catheter 10 can then be easily withdrawn from the bladder and urethra.

While the present invention has been shown and described in terms of a preferred embodiment thereof, it will be understood that this invention is not limited to this particular embodiment and that many changes and modifications may be made without departing from the true spirit and scope of the invention as defined in the appended claims. In addition, as used herein and in the claims, such words as "distal", "proximal", "top", "bottom", "side", and the like are used in conjunction with the drawings for purposes of clarity, and it will be appreciated that they do not limit the device to a particular orientation.

What is claimed is:

1. A urinary catheter for insertion into a patient, comprising:

a distal end, formed from a hollow, relatively rigid, tube;

a proximal end having at least two opposed flexible sections for insertion into the bladder of a patient;

a central section positioned between said distal and proximal ends and consisting of a pair of spaced apart coaxial tubes composed of a collapsible material, an inner one of said coaxial tubes having a lumen extending between respective openings formed in said distal and proximal ends to provide fluid communication therebetween, said central section having an expandable chamber formed between said coaxial tubes, said chamber having a closed end adjacent said proximal end of said catheter and an open passage extending from a portion of said catheter adjacent said distal end;

and valve means coupled to said open passage for selectively introducing a fluid into said chamber and withdrawing the fluid independent of fluid flow through said lumen, wherein said introduction of fluid into said chamber causes stiffening of said central section of said catheter to permit insertion of said catheter into a patient's bladder and subsequent withdrawal of the fluid returns said central section to a substantially flaccid condition and said chamber to a collapsed state.

2. The catheter of claim 1, wherein said tubes of said central section comprise rubber.

3. A urinary catheter for insertion into a patient's bladder, comprising:

a first longitudinally extended hollow tubular member having a proximal end and a distal end, said proximal end having at least a pair of opposed flexible sections for insertion into the bladder of the patient;

a second longitudinally extended hollow tubular member coaxially positioned within said first member and having a plurality of longitudinally extended chambers located about its periphery, said second hollow tubular member being constructed of a substantially non-distensible material and having a lumen extending between respective openings formed in opposing ends thereof to provide fluid communication between said distal and proximal ends of said first hollow tubular member, each of said plurality of chambers having a closed end adjacent said proximal end of said first hollow tubular member and an open passage extending from a portion of said catheter adjacent said distal end of said first hollow tubular member; and, valve means coupled to said open passage for controlling introduction of a fluid into said chambers of said second member independent of fluid flow through said lumen;

whereby a rigidity of said catheter can be varied by varying an amount of the fluid introduced into said chambers of said second member to facilitate insertion of the catheter into the bladder.

4. A urinary catheter for insertion into a patient, comprising:

a distal end, formed from a hollow, relatively rigid, tube;

a proximal end having at least two opposed flexible sections for insertion into the bladder of a patient;

a central section, positioned between said distal and proximal ends, consisting of a pair of spaced apart coaxial tubes composed of a collapsible material having an expandable chamber between said tubes;

valve means for introducing a fluid into said chamber such that introduction of fluid into said chamber causes stiffening of said central section of said catheter to permit insertion of said catheter into a patient's bladder; and, means for separating said at least two sections of said proximal end inside the bladder so as to maintain said catheter within the bladder of the patient.

5. The catheter of claim 4, wherein said separating means comprises a plurality of rods slidably contained within said distal end and said central section and rigidly affixed within said flexible sections of said proximal end, whereby said flexible sections of said proximal end are displaced outwardly when said rods are shifted toward said proximal end of said catheter.

6. The catheter of claim 5, wherein said rods are composed of plastic.

7. The catheter of claim 5, wherein each of said rods contains a first memory area and said central portion contains a plurality of second memory areas corresponding to said first memory areas such that said first and second memory areas cooperate to force said flexible sections of said proximal end apart upon activation of said separating means.

8. A urinary catheter for insertion into a patient's bladder, comprising:

a first hollow tubular member having a proximal end and a distal end, said proximal end having at least two opposed flexible sections for insertion into the patient's bladder;

means for separating said flexible sections inside the bladder so as to maintain said catheter within the bladder;

a second hollow tubular member positioned within said first member and having a plurality of chambers located about its periphery, said second hollow tubular member being constructed of a substantially non-distensible material; and, valve means for controlling the introduction of fluid into said chambers of said second member;

whereby the rigidity of the catheter can be varied by the amount of fluid introduced into said second member to facilitate the insertion of the catheter into the bladder.

9. The catheter of claim 8, further comprising second valve means for controlling introduction of a second fluid into said separating means, whereby introduction of said second fluid into said separating means causes said flexible sections of said proximal end to separate within the bladder when the catheter has been inserted.

10. The catheter of claim 9, wherein said second valve means is connected to said separating means by a hollow hose situated within said second tubular member.

11. The catheter of claim 9, wherein said second fluid comprises a saline solution.

* * * * *